(12) United States Patent
Sagner et al.

(10) Patent No.: US 8,906,306 B2
(45) Date of Patent: Dec. 9, 2014

(54) FLUID TRANSFER CONTROL FOR REAL-TIME PCR

(75) Inventors: Gregor Sagner, Penzberg (DE); Martin Horat, Merlischachen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 475 days.

(21) Appl. No.: 12/748,688

(22) Filed: Mar. 29, 2010

(65) Prior Publication Data

US 2011/0086337 A1 Apr. 14, 2011

(30) Foreign Application Priority Data

Apr. 9, 2009 (EP) .................................... 09005255

(51) Int. Cl.
*G01N 15/06* (2006.01)
*C12P 19/34* (2006.01)

(52) U.S. Cl.
USPC ........................................ 422/68.1; 435/91.2

(58) Field of Classification Search
USPC ........................................ 435/91.2; 422/68.1
See application file for complete search history.

(56) References Cited

U.S. PATENT DOCUMENTS

| 5,736,333 | A | 4/1998 | Livak et al. |
| 7,504,264 | B2 | 3/2009 | Rhode et al. |
| 2004/0136871 | A1 | 7/2004 | Pachl et al. |
| 2005/0232818 | A1 | 10/2005 | Sandell et al. |
| 2007/0141709 | A1 | 6/2007 | Albert et al. |
| 2008/0026483 | A1* | 1/2008 | Oldenburg ..................... 436/174 |
| 2008/0201103 | A1* | 8/2008 | Yang et al. ..................... 702/179 |

FOREIGN PATENT DOCUMENTS

| EP | 0431578 A2 | 6/1991 |
| EP | 1389638 A1 | 2/2004 |
| JP | 2003-004753 A | 1/2003 |
| JP | 2004-016132 A | 1/2004 |
| JP | 2006-010491 A | 1/2006 |
| JP | 2007-017382 A | 1/2007 |
| JP | 2007-046979 A | 2/2007 |
| WO | 2006/099255 A3 | 9/2006 |
| WO | 2007/023205 A1 | 3/2007 |
| WO | 2007/059816 A1 | 5/2007 |

OTHER PUBLICATIONS

Ranade et al. Genome Research (2001) 11: 1262-1268.*
Deniz et al. Proceedings of the National Academy of Sciences, USA (1999) 96: 3670-3675.*
Extended European Search Report issued Aug. 2, 2010 in European Application No. EP 10003757.1.
European Search Report issued Aug. 12, 2009 in European Application No. 09005255.6.

* cited by examiner

*Primary Examiner* — Ardin Marschel
(74) *Attorney, Agent, or Firm* — Dinsmore & Shohl LLP

(57) ABSTRACT

The present invention provides a fluid transfer control method, the method based on measurements of intensities of dyes within the fluid to be transferred. In more detail, the present invention makes use of control dyes and quencher molecules for the fluid transfer controls.

20 Claims, 2 Drawing Sheets

Figure 1

| No | Pos | Incl. | Pip. | Sample | Target 465/510 | Call | Cp | Slope | EPF |
|----|-----|-------|------|--------|----------------|------|-----|-------|-----|
| 385 | Ca01 | ✓ | Pass | Master1 + Target1 | | Positive | 20.95 | 0.0072 | 0.7499 |
| 386 | Ca02 | ✓ | Pass | Master1 + Target1 | | Positive | 20.99 | 0.0639 | 0.7241 |
| 387 | Ca03 | ✓ | Pass | Master1 + Target1 | | Positive | 21.18 | 0.0584 | 0.6502 |
| 388 | Ca04 | ✓ | Pass | Master1 + Target1 | | Positive | 21.02 | 0.0577 | 0.669 |
| 389 | Ca05 | ✓ | Pass | Master1 + Target 0.5 | | Positive | 21.5 | 0.042 | 0.4988 |
| 390 | Ca06 | ✓ | Pass | Master1 + Target 0.5 | | Positive | 21.45 | 0.0378 | 0.4768 |
| 391 | Ca07 | ✓ | Pass | Master1 + Target 0.5 | | Positive | 21.31 | 0.0407 | 0.499 |
| 392 | Ca08 | ✓ | Pass | Master1 + Target 0.5 | | Positive | 21.53 | 0.0423 | 0.5045 |
| 577 | Da01 | ✓ | Pass | Master 0.5 + Target1 | | Positive | 20.59 | 0.0396 | 0.5711 |
| 578 | Da02 | ✓ | Pass | Master 0.5 + Target1 | | Positive | 20.63 | 0.0363 | 0.5309 |
| 579 | Da03 | ✓ | Pass | Master 0.5 + Target1 | | Positive | 20.8 | 0.0319 | 0.475 |
| 580 | Da04 | ✓ | Pass | Master 0.5 + Target1 | | Positive | 20.69 | 0.0317 | 0.4721 |
| 581 | Da05 | ✓ | M-Fail | Master 0 + Target1 | | Negative | | 0.0021 | 0.0234 |
| 582 | Da06 | ✓ | M-Fail | Master 0 + Target1 | | Negative | | 0.001 | 0.0116 |
| 583 | Da07 | ✓ | M-Fail | Master 0 + Target1 | | Negative | | 0.0012 | 0.0123 |
| 584 | Da08 | ✓ | M-Fail | Master 0 + Target1 | | Negative | | 0.0015 | 0.0261 |
| 769 | Ea01 | ✓ | Pass | Master1 + Target 0.5 | | Positive | 21.34 | 0.055 | 0.4843 |
| 770 | Ea02 | ✓ | Pass | Master1 + Target 0.5 | | Positive | 21.93 | 0.0488 | 0.4323 |
| 771 | Ea03 | ✓ | Pass | Master1 + Target 0.5 | | Positive | 21.9 | 0.0478 | 0.4168 |
| 772 | Ea04 | ✓ | Pass | Master1 + Target 0.5 | | Positive | 21.57 | 0.0441 | 0.4088 |
| 773 | Ea05 | ✓ | S-Fail | Master1 + Target 0 | | Negative | | 0.0029 | 0.0119 |
| 774 | Ea06 | ✓ | S-Fail | Master1 + Target 0 | | Negative | | 0 | 0 |
| 775 | Ea07 | ✓ | S-Fail | Master1 + Target 0 | | Negative | | 0.0012 | 0.0301 |
| 776 | Ea08 | ✓ | S-Fail | Master1 + Target 0 | | Negative | | 0.0014 | 0.0257 |
| 961 | Fa01 | ✓ | S-Fail | Master 0.5 + Target 0 | | Negative | | 0 | 0 |
| 962 | Fa02 | ✓ | S-Fail | Master 0.5 + Target 0 | | Negative | | 0.0008 | 0.0037 |
| 963 | Fa03 | ✓ | S-Fail | Master 0.5 + Target 0 | | Negative | | 0.0011 | 0.0039 |
| 964 | Fa04 | ✓ | S-Fail | Master 0.5 + Target 0 | | Negative | | 0.0018 | 0.0468 |
| 965 | Fa05 | ✓ | M-Fail | Master 0 + Target 0 | | Negative | | 0.0027 | 0.0815 |
| 966 | Fa06 | ✓ | M-Fail | Master 0 + Target 0 | | Negative | | 0.0043 | 0.1304 |
| 967 | Fa07 | ✓ | M-Fail | Master 0 + Target 0 | | Negative | | 0.0012 | 0.0205 |
| 968 | Fa08 | ✓ | M-Fail | Master 0 + Target 0 | | Negative | | 0.0013 | 0.0226 |

Samples: 32

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: forward primer GAPDH

<400> SEQUENCE: 1
agccacatcg ctcagacac                                              19

<210> SEQ ID NO 2
<211> LENGTH: 19
<212> TYPE: DNA
<213> ORGANISM: Artificial Sequence
<220> FEATURE:
<223> OTHER INFORMATION: reverse primer GAPDH

<400> SEQUENCE: 2
gcccaatacg accaaatcc                                              19

<210> SEQ ID NO 3
<211> LENGTH: 10
<212> TYPE: DNA
<213> ORGANISM: Artificial Sequence
<220> FEATURE:
<223> OTHER INFORMATION: control oligonucleotide

<400> SEQUENCE: 3
cccaaatcga                                                        10

<210> SEQ ID NO 4
<211> LENGTH: 10
<212> TYPE: DNA
<213> ORGANISM: Artificial Sequence
<220> FEATURE:
<223> OTHER INFORMATION: control oligonucleotide

<400> SEQUENCE: 4
tcgatttggg                                                        10
```

FLUID TRANSFER CONTROL FOR REAL-TIME PCR

SEQUENCE LISTING

The instant application contains a Sequence Listing which has been submitted via EFS-Web and is hereby incorporated by reference in its entirety. Said ASCII copy, created on Mar. 15, 2010 is named 25910US.txt, and is 1,183 bytes in size.

RELATED APPLICATIONS

This application claims priority to EP 09005255.6 filed Apr. 9, 2009, which is hereby incorporated by reference in its entirety.

FIELD OF THE INVENTION

The present invention related to the field of fluid transfer processes used in real-time polymerase chain reactions (PCR). The processes are based on measurements of intensities of dyes within the fluid to be transferred. The methods make use of control dyes and quencher molecules for the fluid transfer controls.

BACKGROUND OF THE INVENTION

For the preparation of assays in most of the cases several fluid reagents need to be mixed, and for reproducible results of said assays it is of importance that a controlled volume of each reagent and the sample is transferred. Since all fluid transfer processes have a certain variance, transfer errors can not be avoided, but at least it must be possible to detect those transfer processes with unacceptable errors in order to neglect the result of these assays.

Especially real-time PCR systems require an exact mixture of all reaction components for reliable and comparable quantification because the amount of sample material, of primers/probes as well as of master mixes required for real-time PCR particularly influence the quantification result. But of course, other assays also require a set-up with mixing of several components, and a control of said set-up in terms of volume transfer is of importance, too.

To address these uncertainties, normalization techniques can be used, and mainly two different normalization methods are established for quantitative real-time PCR (qPCR):
(1) To normalize against differences of the sample material (DNA or RNA), an unregulated reference gene is measured in combination with the target gene, and the ratio of target/reference is calculated (Relative Quantification method, see, e.g., LightCycler 480 operator's manual, page 179ff).
(2) To normalize against fluorescence intensity differences, a reference dye (not participating in the qPCR reaction) is added, and all measured fluorescence values are normalized against the reference dye fluorescence (Applied Biosystems, ROX reference dye, U.S. Pat. No. 5,736,333).

But both of these normalization methods exhibit problems. The normalization method (1) can only control the amount/quality of the sample material when relative quantification is applied, not when absolute quantification is used. Furthermore, this method does not control the amount of any other PCR component besides the sample material. The normalization method (2) only normalizes against fluorescence intensity differences generated by qPCR system variations. It does not control or warn the user when the amount of a certain component is below a certain limit.

Currently, there are no fluid transfer control systems known in the state of the art that provide a control system for the volumes of the components to be mixed for an assay set-up.

The present invention provides a closed system for assay set-up that encompasses control strategies to identify volume errors of components mixed for said assays. The method according to the present invention is especially suitable for the set-up of real-time PCR amplifications.

SUMMARY OF THE INVENTION

One aspect of the present invention is a fluid transfer control method, the method comprising
a) providing a solution to be transferred with a control dye,
b) transferring pre-defined volumes of said solution comprising a concentration of said control dye to a plurality of vessels,
c) measuring the intensity of the control dyes within each vessel,
d) comparing the intensity measured in step c) for each vessel with a pre-defined threshold value, whereas a fluid transfer error is detected for a certain vessel, if the intensity measured in step c) is below said pre-defined threshold value,
e) compiling a mean intensity value of all vessels having an intensity measured in step c) that is above said pre-defined threshold value,
f) verifying for all vessels having an intensity measured in step c) that is above said pre-defined threshold value, if said intensity is within a pre-defined range surrounding said mean intensity value compiled in step e), wherein a fluid transfer error is detected for a certain vessel, if the intensity measured in step c) is not within said range, and
g) declaring a correct fluid transfer for all vessels having an intensity measured in step c) that is within said pre-defined range of step f).

"Solution" is used throughout the present invention as generic term for all kinds of liquid components that need to be transferred into a vessel for a subsequent reaction in said vessel, wherein said reaction may need additional components to be added to said vessel. Consequently, the method according to the present invention can be applied for each of the transfer steps that need to be performed prior to said reaction. If more than one solution is transferred to one reaction vessel, each of said solutions may be mixed with a different, distinguishing dye. Alternatively, each solution can have the same dye, and the change of intensity after each step can be used for the transfer control.

Throughout the present invention the control dyes are used as transfer controls. The presence of the control dyes can be measured using suitable machinery depending on the used dyes, e.g., PMTs or CCD chips for optical dyes or scintillation counters in case of radioactive dyes.

The measured intensities are processed by a software module and said software module compares the calculated values with certain thresholds (e.g., minimum fluorescence, range of deviation from a mean value). The software module generates an output signal that either (a) warns the user that certain vessel failed the transfer control check ("soft closing") or (b) inhibits result calculation of vessels failing the transfer control ("hard closing"). Moreover, the software module can be used to avoid the further processing of the vessels with a detected transfer error.

An advantage of the present invention is the independent check of transfer volume correctness for all components that are required for a certain application in an automated fashion. Particularly, when automatic liquid handling systems (pipetting robots) are used for the reaction setup, no manual control by eye is applicable to the process. Furthermore, controlling the transfer process in low volume applications (total reaction volume <3 μl) is of especial relevance as liquid handling of (sub-) microliter volumes is highly critical concerning accuracy and reproducibility.

Another aspect of the present invention is a fluid transfer control method in a real-time PCR amplification workflow, the method comprising i) providing a solution to be transferred with a control dye,
 ii) transferring pre-defined volumes of said solution comprising a concentration of said control dye to a plurality of vessels,
 iii) measuring the intensity of the control dyes within each vessel,
 iv) comparing the intensity measured in step iii) for each vessel with a pre-defined threshold value, wherein a fluid transfer error is detected for a certain vessel, if the intensity measured in step iii) is below said threshold value, and
 v) performing a real-time PCR amplification in said plurality of vessels, wherein the results of real-time PCR amplifications performed in those vessels with a detected fluid transfer error in step iv) are marked accordingly.

Alternatively, the fluid transfer control method in a real-time PCR amplification workflow according to the present invention can also be preformed with step v') performing a real-time PCR amplification in those vessels without a detected fluid transfer error in step iv)

instead of step v).

Since real-time PCR amplification requires several components, each component may contain the same or different dyes as transfer controls. Before the real-time PCR reaction is started, the intensity of each dye is measured using a real-time PCR instrument. E.g., one control dye is contained in the qPCR master mix, the second control dye is contained in the sample material and a third control dye is contained in the primer/probes mixture.

BRIEF DESCRIPTION OF THE FIGURES

FIG. 1 Screenshot of the software executing the method according to the present invention illustrating the transfer control result of a plurality of vessels.

DETAILED DESCRIPTION OF THE INVENTION

Figure 2:
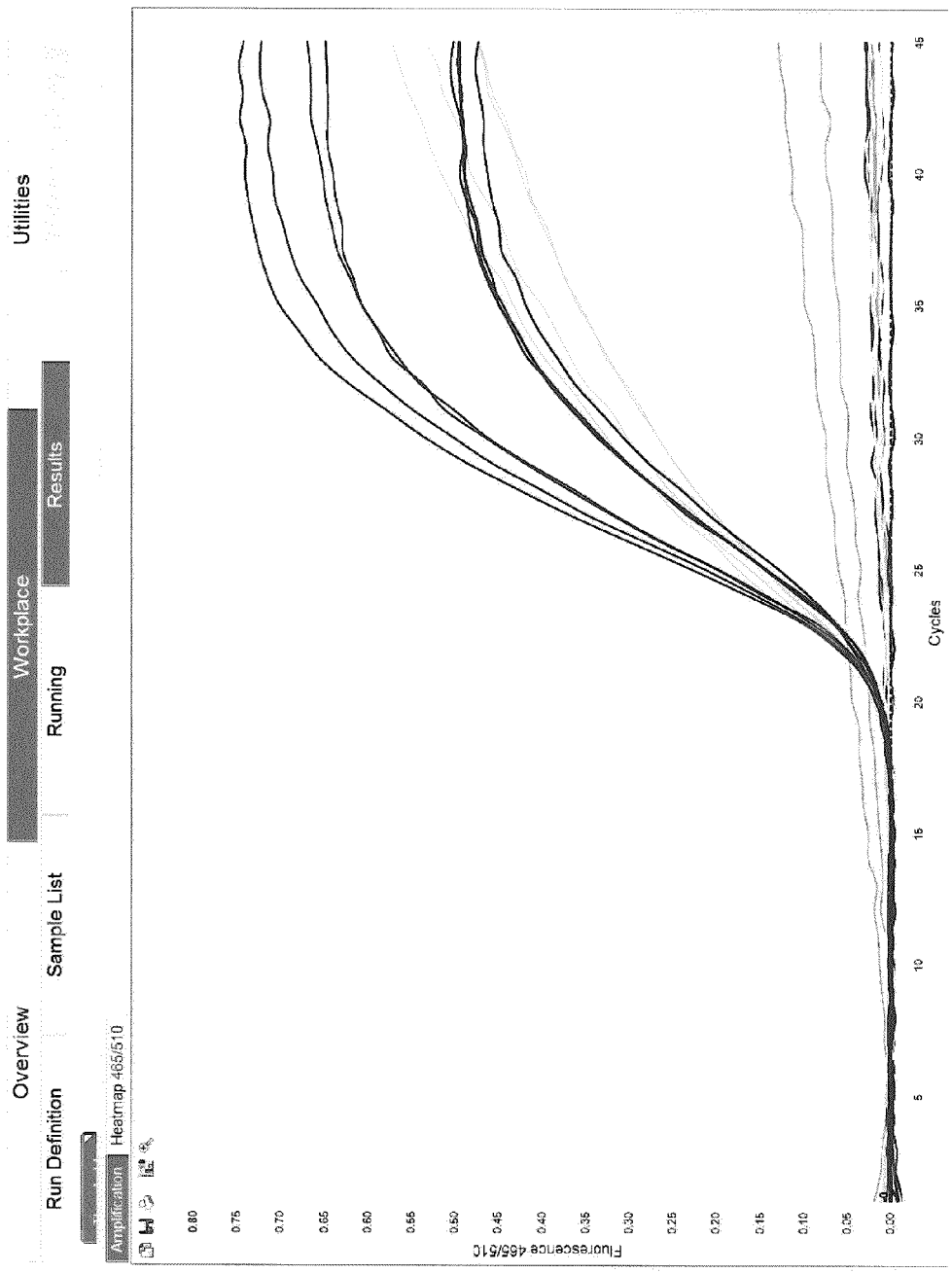
FIG. 2 Screenshot of the software executing the PCR-embodiment of the method according to the present invention illustrating the output of PCR amplification curves of a plurality of vessels.

One aspect of the present invention is a fluid transfer control method, the method comprising a) providing a solution to be transferred with a control dye,
 b) transferring pre-defined volumes of said solution comprising a concentration of said control dye to a plurality of vessels,
 c) measuring the intensity of the control dyes within each vessel,
 d) comparing the intensity measured in step c) for each vessel with a pre-defined threshold value, wherein a fluid transfer error is detected for a certain vessel, if the intensity measured in step c) is below said pre-defined threshold value,
 e) compiling a mean intensity value of all vessels having an intensity measured in step c) that is above said pre-defined threshold value,
 f) verifying for all vessels having an intensity measured in step c) that is above said pre-defined threshold value, if said intensity is within a pre-defined range surrounding said mean intensity value compiled in step e), wherein a fluid transfer error is detected for a certain vessel, if the intensity measured in step c) is not within said range, and
 g) declaring a correct fluid transfer for all vessels having an intensity measured in step c) that is within said pre-defined range of step f).

In a preferred fluid transfer control method according to the present invention, said plurality of vessels are arranged as a multiwell plate, said multiwell plate has at least 8 wells, preferably at least 96 wells, more preferably at least 384 wells, most preferably at least 1536 wells.

Alternatively, the person skilled in the art will appreciate that an arrangement of separate vessels in a holding rack are equally suitable for the present invention. Of course it is possible throughout the present invention that some of the wells of a multiwell plate are left empty and not each of the plurality of vessels receive a fluid transfer.

In yet another preferred fluid transfer control method according to the present invention, said threshold value of step d) is pre-defined based on measured intensity values using a reference solution, said reference solution having the volume and the control dye concentration of step b).

The threshold value is used as a first transfer control in order to detect vessels without any solution and consequently without any intensity as well as vessels that obtained only a minor portion of the pre-defined volume. In order to figure out a suitable threshold value, it is preferred to perform a reference measurement with a solution having the volume and the dye concentration of the pre-defined fluid transfer process, whereas the measured intensity can be used as the threshold value.

Alternatively, the background intensity of empty vessels can be used to define the pre-defined threshold value, e.g., the threshold value can be defined as three time the background intensity.

Since minor transfer variances may be acceptable, it is more preferred to allow a certain deviation of measured intensity, e.g., of about 10%. In this example, a transfer error of 10% is still acceptable. Depending on the measured intensity the vessel will be flagged as "transfer control passed" or "transfer control failed".

In addition to this first transfer control a second transfer control is performed to evaluate the deviation between the vessels, because said deviations pose problems with regard to meaningful comparisons of said vessels. Said second pipetting control is based on a pre-defined range surrounding the mean intensity value of all vessels that passed the first pipetting control. Depending on the measured intensity, the vessel will be flagged as "range control passed" or "range control failed".

This second pipetting control is of particular importance in situations with a high variance of the solution to be transferred between each use of the method. This variance of the solution to be transferred may originate from an volume off-set between subsequent applications of the method or from a shift of the control dye concentration. In such a situation it is not possible to set a meaningful threshold for the mean value to be applied for each use of the method.

Therefore, the present invention provides a possibility for automated pipetting control based only on the actual transfer run without the need for another pre-defined threshold value, because the mean intensity value is determined for each run to identify comparable vessels.

In combination with the first transfer control it is guaranteed that no vessels with transfer volumes far from the defined amount are used for determining the mean intensity value, because these vessels would severely distort the value of the second control.

Mainly, there are two different suitable embodiments for using such a range surrounding the mean intensity value.

A preferred fluid transfer control method according to the present invention is a method, wherein said pre-defined range of step f) is symmetrically surrounding said mean intensity value compiled in step e).

Another preferred fluid transfer control method according to the present invention is a method, wherein said pre-defined range of step f) is asymmetrically surrounding said mean intensity value compiled in step e).

These two embodiments reflect different situations of acceptable variances. In situations, where precession towards lower and higher transfer volumes are of equal importance, a symmetrical range should be used, whereas the width of said range is pre-defined based on acceptable transfer variances. In situations, where variances, e.g., towards higher volumes are not critical, it is preferred to use an asymmetrical range having a small sub-range for smaller volumes and a larger sub-range for higher volumes.

If more than one solution needs to be transferred into each vessel, also for the other solutions a control can be used within the scope of the present invention. For one embodiment, the other solutions will be mixed with a control dye, too. Throughout the present invention it is possible to use the same control dye for each solution, if the solutions are added one after the other to the vessels and if after adding of each solution the intensity is measured. Therefore, the transfer control in this embodiment is based on the intensity increase of the control dye after adding a certain solution. Alternatively, each solution can be mixed with a different control dye, such that said dyes are spectrally distinguishable. Consequently, in this embodiment the solutions can be added all at once or one after the other to the vessels, because the intensities of all dyes can be measured independently.

If two solutions need to be added to the vessels, a preferred method according to the present invention uses a control dye for the first and a quencher molecule for the second solution. This setup has the advantage that two transfer controls can be established with only one dye, such that the machinery to measure the intensity is less complex compared to a setup requiring two dyes.

A preferred fluid transfer control method according to the present invention is a method, wherein pre-defined volumes of a second solution comprising a concentration of a quencher molecule is added to the vessels and wherein said quencher molecule quenches the intensity of said control dye used in step a), said method comprises the additional steps
h) measuring the quenched intensity of the control dyes within each vessel,
i) calculating a quenching parameter value based on the quenched intensity measured in step h) for each vessel, wherein a fluid transfer error for a certain vessel is detected, if a pre-defined quenching threshold criterion of said quenching parameter value is not fulfilled,
j) compile a mean quenching parameter value of all vessels having a quenching parameter value calculated in step i) that fulfills said pre-defined quenching threshold criterion,
k) verifying for all vessels having a quenching parameter value calculated in step i) that fulfills said pre-defined quenching threshold criterion, if said quenching parameter value is within a pre-defined second range surrounding said mean quenching parameter value compiled in step j), whereas a fluid transfer error is detected for a certain vessel, if said quenching parameter value measured in step i) is not within said pre-defined second range, and
l) declaring a correct second fluid transfer for all vessels having a quenching parameter value measured in step i) that is within said pre-defined second range of step k).

In this embodiment the second fluid transfer control is again based on two control steps, namely the "transfer control" and the "range control" as described above. Since the steps h)-l) are subsequent to steps a)-g), there are two different embodiments that are possible within the scope of the present invention.

In a preferred fluid transfer control method according to the present invention, the steps h)-l) are only performed for vessels without a detected fluid transfer error in step d).

In another preferred fluid transfer control method according to the present invention, the steps h)-l) are only performed for vessels declared as having a correct fluid transfer in step g).

Depending on the application of the method according to the present invention, it may be preferred to perform the second fluid transfer only if one or both transfer controls of the first fluid transfer were passed. On the other hand, if it is more reasonable to run the entire workflow even with failed vessels than to stop the workflow only for a certain amount of vessels, the vessels are at least flagged with the respective errors.

For the first transfer control of the second fluid transfer a quenching parameter value is calculated to be compared with pre-defined quenching threshold criterion. The quenching parameter is based on the quenched intensity measured in step h) and mainly there are two major embodiments of such a quenching parameter, namely said parameter is the measured quenched intensity as such or said parameter is a ratio compiled using the control dye intensity and the quenched intensity.

In a preferred fluid transfer control method according to the present invention, said quenching parameter value for each vessel is the quenched intensity of the control dyes measured in step h).

In a more preferred fluid transfer control method according to the present invention, a fluid transfer error for a certain vessel is detected in step i), if the quenched intensity of the control dyes measured in step h) is above a pre-defined quenched threshold value.

In another preferred fluid transfer control method according to the present invention, said calculated quenching parameter value of step i) is a ratio of the intensity of the control dyes measured in step c) and the quenched intensity of the control dyes measured in step h).

In another more preferred fluid transfer control method according to the present invention, a fluid transfer error for a certain vessel is detected in step i), if said ratio is below or above a pre-defined quenched threshold ratio.

A transfer error of the second solution is equal to a small amount of quencher molecules in the vessel and consequently, the quenched intensity measured will be higher than expected. Therefore, in case of a pipetting error the ratio of the intensity of the control dyes measured in step c) divided by the quenched intensity of the control dyes measured in step h) will be smaller than the pre-defined quenched threshold ratio. On the other hand, the ratio of the quenched intensity of the control dyes measured in step h) divided by the intensity of the control dyes measured in step c) must be larger than the pre-defined quenched threshold ratio to detect a pipetting error.

As discussed with respect to the threshold and the range of the first fluid transfer, also the pre-defined quenching threshold criterion is based on measurements using reference solutions and of course two reference solutions are required for this embodiment.

Again, also said pre-defined quenching threshold criterion can be defined empirically using intensities of empty vessels and intensities of vessels having no quencher molecules.

In a preferred fluid transfer control method according to the present invention, said pre-defined quenching threshold criterion is based on measurements using two reference solutions, a first reference solution having the volume and the control dye concentration of step b) and the second reference solution having the volume and the quencher dye concentration to be used in the fluid transfer of said second solution.

Also with regard to said second range there are two different embodiments for its setup and the discussion above relating to the first range applies here, too.

In another preferred fluid transfer control method according to the present invention, said pre-defined second range of step k) is symmetrically surrounding said mean quenching parameter value of step j) and the width of said second range is pre-defined based on acceptable transfer variances.

In yet another preferred fluid transfer control method according to the present invention, said pre-defined second range of step k) is asymmetrically surrounding said mean quenching parameter value of step j) and the said asymmetrical second range is pre-defined based on different acceptable transfer variances towards lower or higher transfer volumes.

With respect to the succession of the different steps of the method according to the present invention, there are two different alternatives for adding the second solution.

In a preferred fluid transfer control method according to the present invention, said pre-defined volume of a second solution comprising a quencher molecule is added to the vessels after step g) and prior to step h).

In another preferred fluid transfer control method according to the present invention, said pre-defined volume of a second solution comprising a quencher molecule is added to the vessels prior to step c).

Therefore, for the first alternative, namely adding of the second solution after the controls of the first fluid transfer are finalized, the measurement of the intensity of the control dye is performed prior to the presence of the quencher molecule.

For the second alternative, both solutions are mixed prior to performing both fluid transfer controls and consequently, the control dye and the quencher molecule are present in the vessels for both control measurements. This setup of the method according to the present invention is possible, if the quenching of the control dye can be switched on and off within said vessels In a more preferred fluid transfer control method according to the present invention, said intensity of the control dyes in step c) and said quenched intensity of the control dyes in step h) are measured successively within said vessels based on adjusting a solution parameter to switch between a quenched and a non-quenched state of the control dyes.

Such that a quencher molecule is able to quench the intensity of the control dyes, the quencher molecule needs to be in close proximity to the control dye and consequently, the quencher molecule must have the affinity to bind to the control dye. Therefore, in order to avoid the binding of the quencher molecule to the control dye, it must be possible to overcome said affinity within the solution of the vessels. Depending on the kind of interaction between the quencher molecule and the control dye, the person skilled in the art will know about procedures to avoid said interaction.

In another more preferred fluid transfer control method according to the present invention, said solution parameter is the solution temperature.

In yet another more preferred fluid transfer control method according to the present invention, said solution parameter is the solution molarity or the solution pH.

In addition to the affinity of the quencher molecule and the control dye mentioned above, it is of importance that the emission of the control dye and the absorbance of the quencher molecule are spectrally adjusted to each other. If the overlap between the emission spectra and the absorbance spectra is not thorough enough, the quenching will become insufficient.

In still another preferred fluid transfer control method according to the present invention, said quencher molecule and said control dye are spectrally adjusted such that the intensity of the control dye is effectively quenched by said quencher molecule.

On the other hand, it is possible to use a quencher molecule having an absorbance spectra that only quenches a part of the emission spectra of the control dye and consequently, the measurement of the control dye intensity as well as of the quenched intensity is performed only within the frequency spectra corresponding to the absorbance spectra of the quencher molecule.

In another preferred fluid transfer control method according to the present invention, said control dye is a fluorescence dye.

Without limiting the scope of the present invention, the method of the present invention is especially suitable for the fluid transfer processes for preparing real-time PCR amplifications. For such a real-time PCR several components are to be mixed, namely the sample to be amplified, a master mix comprising a polymerase and nucleotides as well as the detection mix comprising primers and probes. As an example of a suitable fluid transfer protocol according to the present invention, the master mix comprising the control dye is mixed with the detection mix and said mixture is transferred to the vessels performing the first fluid transfer control. Afterwards, the sample comprising the quencher molecule is added to said vessels performing the second fluid transfer control. Alternatively, it is of course possible to use samples comprising the control dye and a master mix comprising the quencher molecule. Moreover, it is possible to also control the mixing of master and detection mix by using a second control dye added to the detection mix.

In a preferred fluid transfer control method according to the present invention, said solution is transferred according to steps a)-g) for a subsequent real-time PCR amplification containing a detection dye.

In another preferred fluid transfer control method according to the present invention, said solutions are transferred according to steps a)-l) for a subsequent real-time PCR amplification containing a detection dye.

If the method according to the present invention is applied for a fluid transfer control during preparation of a real-time PCR, it is of importance to take into account that the emission spectra of the detection dye required for the online monitoring of the PCR amplification is not affected by the control dye.

In a more preferred fluid transfer control method according to the present invention, said control dye is spectrally separated from said detection dye.

In another more preferred fluid transfer control method according to the present invention, said control dye and said detection dye are fluorescence dyes.

Without limiting the scope of the present invention, a preferred embodiment of the method according to the present invention is based on oligonucleotides as affinity tags at both the control dye as well as at the quencher molecule.

In a preferred fluid transfer control method according to the present invention, said control dye is attached to an oligonucleotide.

In another preferred fluid transfer control method according to the present invention, said quencher molecule is attached to a second oligonucleotide.

If the oligonucleotides attached to the control dye and the quencher molecule should have affinity to each other, their sequences must be at least partially complementary.

In a more preferred fluid transfer control method according to the present invention, said oligonucleotide and said second oligonucleotide have complementary sequences.

The usage of oligonucleotides as affinity tags has the additional advantage that the quenching of the control dye can easily be switched off and on by increasing or decreasing the solution temperature above or below the melting temperature of the hybridization of the oligonucleotide and the second oligonucleotide, respectively.

Another aspect of the present invention is a fluid transfer control method in a real-time PCR amplification workflow, the method comprising
  i) providing a solution to be transferred with a control dye,
  ii) transferring pre-defined volumes of said solution comprising a concentration of said control dye to a plurality of vessels,
  iii) measuring the intensity of the control dyes within each vessel,
  iv) comparing the intensity measured in step iii) for each vessel with a pre-defined threshold value, wherein a fluid transfer error is detected for a certain vessel, if the intensity measured in step iii) is below said threshold value, and
  v) performing a real-time PCR amplification in said plurality of vessels, wherein the results of real-time PCR amplifications performed in those vessels with a detected fluid transfer error in step iv) are marked accordingly.

In another embodiment of the a fluid transfer control method in a real-time PCR amplification workflow according to the present invention step v) is replaced by
  v') performing a real-time PCR amplification in those vessels without a detected fluid transfer error in step iv).

A preferred fluid transfer control method in a real-time PCR amplification workflow according to the present invention is a method, wherein pre-defined volumes of a second solution comprising a concentration of a quencher molecule is added to the vessels prior to step v) and wherein said quencher molecule quenches the intensity of said control dye used in step i), said method comprises the additional steps performed prior to step v)
  A) measuring the quenched intensity of the control dyes within each vessel,
  B) calculating a quenching parameter value based on the quenched intensity measured in step A) for each vessel,
  wherein a fluid transfer error for a certain vessel is detected, if a pre-defined quenching threshold criterion of said quenching parameter value is not fulfilled,
  C) compile a mean quenching parameter value of all vessels having a quenching parameter value calculated in step B) that fulfills said pre-defined quenching threshold criterion,
  D) verifying for all vessels having a quenching parameter value calculated in step B) that fulfills said pre-defined quenching threshold criterion, if said quenching parameter value is within a pre-defined second range surrounding said mean quenching parameter value compiled in step C), wherein a fluid transfer error is detected for a certain vessel, if said quenching parameter value measured in step B) is not within said pre-defined second range, and
  E) declaring a correct second fluid transfer for all vessels having a quenching parameter value measured in step B) that is within said pre-defined second range of step D).

Example 1

Preparation of Master Mix and Target DNA Mix Containing Pipetting Control Components A) A 2-fold master mix for real-time PCR of the GAPDH gene from human cDNA was prepared containing the following components:
  1 µM of human GAPDH primers according to SEQ ID NO: 1 and SEQ ID NO: 2
  800 nM of a human GAPDH UPL probe (Universal Probe Library, Probe #60, Roche Applied Science, Cat. No. 04 688 589 001)
  PCR components of the RealTime ready DNA Master, Probes (Roche Applied Science) were used. The master mix contains 4 µM oligonucleotide according to SEQ ID NO: 3 terminally labeled at the 5'-end with a long wavelength fluorescent dye (JA286, Roche Applied Science; excitation maximum at 686 nm, emission maximum at 703 nm).

B) A 2-fold target DNA mix for real-time amplification was prepared containing the following components:
  1 ng of human cDNA (qPCR Human Reference cDNA, Clontech, Cat. No. 639654)
  4 µM oligonucleotide according to SEQ ID NO: 4 terminally labeled at the 3'-end with a non-fluorescent quencher (Dabsyl, Roche Applied Science, WO 2007/059816).

The two oligonucleotides according to Seq ID No. 3 and 4 are complementary.

Example 2

Preparation of a Multiwell Real-Time PCR Plate Containing Different Amounts of Master Mix and Target DNA Mix Eight different combinations of master mix and target DNA mix were filled into a 1536-well real-time PCR plate (Roche Applied Science) using a Nanodrop Express liquid handling robot (Innovadyne, Part Nos. 12043 (Fluidics Module) and 11245 (Stage Module).

| Combination | 2x Master mix (μl) | 2x Target DNA mix (μl) |
|---|---|---|
| 1 | 1 | 1 |
| 2 | 0.5 | 0.5 |
| 3 | 0.5 | 1 |
| 4 | 0 | 1 |
| 5 | 1 | 0.5 |
| 6 | 1 | 0 |
| 7 | 0.5 | 0 |
| 8 | 0 | 0 |

Each combination was tilled into 96 positions of the 1536-well plate representing technical replicates.

Example 3

Real-Time PCR Including a Pipetting Control Measuring Step

Real-time amplification and pipetting control measurements were performed on a LightCycler 1536 instrument with analysis software (Roche Applied Science). The software was written in programming language Microsoft .Net C#.

The pipetting control measurement was performed before the amplification was performed according to the following protocol.

A) Pipetting Control Measurement:

Two single acquisitions were performed using the filter combination 618 (excitation)/660 (emission).

|  | Temp. (° C.) | Hold Time (sec) | Ramp Rate (° C./sec) | Acquisition | Cycles | Detection Mode | Quant. Factor |
|---|---|---|---|---|---|---|---|
| 1. acquisition | 55 | 30 | 4.8 | single | 1 | dynamic | 1.2 |
| 2. acquisition | 37 | 30 | 2.5 | single | 1 | dynamic | 1.2 |

B) Real-Time PCR:

Real-time amplification was performed using the filter combination 465 (excitation)/510 (emission).

|  | Temp. (° C.) | Hold Time (sec) | Ramp Rate (° C./sec) | Acquisition | Cycles | Detection Mode | Quant. Factor |
|---|---|---|---|---|---|---|---|
| denaturation | 95 | 60 | 4.8 | none | n.a. | n.a. | n.a. |
| amplification | 95 | 1 | 4.8 | none | 45 | n.a. | n.a. |
|  | 60 | 60 | 2.5 | single |  | dynamic | 2.0 |
| cooling | 40 | 30 | 2.5 | none | n.a. | n.a. | n.a. |

Example 4

Fluid Transfer Status Calculation for Individual Real-Time PCR Reaction Wells

The fluorescence intensity of each well at 55° C. was compared to a predefined minimum fluorescence threshold value saved in the configuration file of the software. The predefined threshold value was determined empirically by analyzing the auto fluorescence of empty wells of 1536-well real-time PCR plates. The threshold value was set significantly above the highest measured value of an empty well. The threshold value was set to 5 fluorescence units as defined by the prototype software.

All plate positions with a fluorescence value below that threshold were set to the fluid transfer error status "M-Fail" (master mix fluid transfer failed). The result is shown in FIG. 1 for samples of combinations 4 and 8 (see table of example 2).

For all plate positions above that fluorescence threshold, the ratio of fluorescence at 55° C. divided by fluorescence at 37° C. was calculated. The calculated ratio was compared to a predefined minimum ratio threshold value saved in the configuration file of the software. The predefined ratio threshold value was determined empirically by analyzing the ratios of empty wells and wells not containing a quencher oligonucleotide (SEQ ID NO: 4) of 1536-well real-time PCR plates. The ratio threshold value was set significantly above the highest measured ratio value of wells not containing quencher oligonucleotides. The ratio threshold value was set to 1.5.

All plate positions with a ratio below that minimum ratio threshold were set to the fluid transfer error status "S-Fail" (setup failed, i.e., target DNA fluid transfer failed). The result is shown in FIG. 1 for samples of combinations 6 and 7 (see table of example 2).

For all plate positions above that minimum ratio threshold, a mean ratio value is calculated and compared to a predefined ratio range saved in the configuration file of the software. The predefined ratio range was determined empirically by comparing PCR performance of fluid transfer variances and was set asymmetrically around the mean ratio value. The acceptance range was set to 100% above the mean ratio value and 50% below the mean ratio value.

All plate positions with a ratio outside that range were set to the fluid transfer error status "S-Fail" (setup failed, i.e., target DNA fluid transfer failed).

All plate positions with a fluorescence value above the predefined minimum fluorescence threshold, above the predefined minimum ratio threshold and within the predefined ratio range were set to the fluid transfer status "Pass". The result is shown in FIG. 1 for samples of combinations 1, 2, 3 and 5.

Example 5

Display of Fluid Transfer Control Results Combined with Real-Time PCR Results

The status of the fluid transfer control is displayed within the real-time PCR result table (FIG. 1). Sorting and filtering allows the user to select for a certain fluid transfer control status and to discriminate valid from invalid real-time PCR reactions. As can be seen in FIG. 1, samples displaying the fluid transfer control status "Pass" do also display a positive call and a valid Cp value. Samples displaying the fluid transfer control status "Fail" (M-Fail or S-Fail) do display a negative call and no Cp value due to the intended setup of the master mix and target DNA mix combinations.

The result table is combined with real-time amplification curves (FIG. 2). As can be seen in FIG. 2, samples displaying the fluid transfer control status "Pass" do also display positive amplification curves. Samples displaying the fluid transfer control status "Fail" (M-Fail or S-Fail) do display negative amplification curves due to the intended setup of the master mix and target DNA mix combinations.

What is claimed is:

1. A fluid transfer control method, the method comprising the steps of:
   providing a solution comprising a concentration of a control dye,
   transferring a pre-defined volume of the solution comprising the control dye to each of a plurality of vessels,
   measuring an intensity of the control dye within each vessel,
   comparing the intensity measured for each vessel with a pre-defined threshold value, whereby a fluid transfer error is detected for a vessel and the vessel is excluded from further analysis if the measured intensity is below the pre-defined threshold value,
   compiling a mean intensity value of all vessels having a measured intensity that is above the pre-defined threshold value,
   verifying for each vessel having a measured intensity that is above the pre-defined threshold value, if the intensity is within a pre-defined range surrounding the compiled mean intensity value, wherein a fluid transfer error is detected for a vessel and the vessel is excluded from further analysis if the measured intensity is not within the pre-defined range, and
   declaring a correct fluid transfer for each vessel having a measured intensity that is within the pre-defined range,
   transferring a pre-defined volume of a second solution comprising a concentration of a quencher molecule to each of the vessels declared as having a correct fluid transfer, wherein the quencher molecule quenches the intensity of the control dye,
   measuring a quenched intensity of the control dye within each vessel, calculating a quenching parameter value based on the measured quenched intensity for each vessel, wherein a fluid transfer error for a vessel is detected and the vessel is excluded from further analysis if a pre-defined quenching threshold criterion of the quenching parameter value is not fulfilled, compiling a mean quenching parameter value of all vessels having a calculated quenching parameter value that fulfills the pre-defined quenching threshold criterion, if the quenching parameter value is within a pre-defined second range surrounding the compiled mean quenching parameter value, whereby a fluid transfer error is detected for a vessel and a vessel is excluded from further analysis if the measured quenching parameter value is not within the pre-defined second range, and declaring a second correct fluid transfer for each vessel having a measured quenching parameter value that is within the pre-defined second range.

2. The fluid transfer control method of claim 1, wherein the plurality of vessels is arranged as a multiwell plate having at least 8 wells.

3. The fluid transfer control method of claim 1, wherein the plurality of vessels is arranged as a multiwell plate having at least 96 wells.

4. The fluid transfer control method of claim 1, wherein the plurality of vessels is arranged as a multiwell plate having at least 384 wells.

5. The fluid transfer control method of claim 1, wherein the plurality of vessels is arranged as a multiwell plate having at least 1536 wells.

6. The fluid transfer control method of claim 1, wherein the pre-defined threshold value is based on measured intensity values using a reference solution, the reference solution having a volume and a control dye concentration equal to those of the solution transferred in the transfer step.

7. The fluid transfer control method of claim 1, wherein the calculated quenching parameter value is a ratio of the intensity of the measured control dye and the intensity of the measured quenched control dye.

8. The fluid transfer control method of claim 1, wherein the pre-defined quenching threshold criterion is based on measurements using two reference solutions, a first reference solution having a volume and a control dye concentration equal to those in the step of transferring the solution comprising the control dye, and the second reference solution having a volume and a quencher molecule concentration equal to those in the step of transferring a second solution comprising a quencher molecule.

9. The fluid transfer control method of claim 1, wherein the pre-defined volume of a second solution comprising a quencher molecule is transferred to the vessels prior to the step of measuring an intensity of the control dye.

10. The fluid transfer control method of claim 1, wherein the intensity of the control dye and the quenched intensity of the control dye are measured successively within each vessel after adjusting a solution parameter to switch between a quenched and a non-quenched state of the control dye.

11. A method for controlling transfer of a solution to a plurality of vessels for subsequent real-time PCR amplification in the vessels, the method comprising the steps of:

providing a solution comprising a concentration of a control dye, wherein the solution also comprises a detection dye for the subsequent PCR amplification, transferring a pre-defined volume of the solution comprising the control dye to each of a plurality of vessels, measuring an intensity of the control dye within each vessel, comparing the intensity measured for each vessel with a pre-defined threshold value, whereby a fluid transfer error is detected for a vessel and the vessel is excluded from further analysis if the measured intensity is below the pre-defined threshold value, compiling a mean intensity value of all vessels having a measured intensity that is above the pre-defined threshold value, verifying for each vessel having a measured intensity that is above the pre-defined threshold value, if the intensity is within a pre-defined range surrounding the compiled mean intensity value, wherein a fluid transfer error is detected for a vessel and excluding the vessel from further analysis if the measured intensity is not within the pre-defined range, declaring a correct fluid transfer for each vessel having a measured intensity that is within the pre-defined range, and declaring an incorrect fluid transfer for each vessel in which a fluid transfer error is detected for the vessel; and subsequently performing the real-time PCR amplification in the plurality of vessels and marking accordingly results of the amplifications performed in vessels wherein an incorrect fluid transfer is declared, or subsequently performing the real-time PCR amplification in vessels only wherein a correct fluid transfer is declared.

12. A method for controlling transfer of a solution to a plurality of vessels for subsequent real-time PCR amplification in the vessels, the method comprising the steps of:

providing a solution comprising a concentration of a control dye, wherein the solution also comprises a detection dye for the subsequent PCR amplification, transferring a pre-defined volume of the solution comprising the control dye to each of a plurality of vessels, measuring an intensity of the control dye within each vessel, comparing the intensity measured for each vessel with a pre-defined threshold value, whereby a fluid transfer error is detected for a vessel if the measured intensity is below the pre-defined threshold value, compiling a mean intensity value of all vessels having a measured intensity that is above the pre-defined threshold value, verifying for each vessel having a measured intensity that is above the pre-defined threshold value, if the intensity is within a pre-defined range surrounding the compiled mean intensity value, wherein a fluid transfer error is detected for a vessel if the measured intensity is not within the pre-defined range, declaring a correct fluid transfer for each vessel having a measured intensity that is within the pre-defined range, transferring a pre-defined volume of a second solution comprising a concentration of a quencher molecule to each of the vessels, wherein the quencher molecule quenches the intensity of the control dye, measuring a quenched intensity of the control dye within each vessel, calculating a quenching parameter value based on the measured quenched intensity for each vessel, wherein a fluid transfer error is detected for a vessel if a pre-defined quenching threshold criterion of the quenching parameter value is not fulfilled, compiling a mean quenching parameter value of all vessels having a calculated quenching parameter value that fulfills the pre-defined quenching threshold criterion, verifying for each vessel having a calculated quenching parameter value that fulfills the pre-defined quenching threshold criterion, if the quenching parameter value is within a pre-defined second range surrounding the compiled mean quenching parameter value, whereby a fluid transfer error is detected for a vessel if the measured quenching parameter value is not within the pre-defined second range, declaring a second correct fluid transfer for each vessel having a measured quenching parameter value that is within the pre-defined second range, and declaring an incorrect fluid transfer for each vessel in which a fluid transfer error is detected for the vessel; and subsequently performing the real-time PCR amplification in the plurality of vessels and marking accordingly results of the amplifications performed in vessels wherein an incorrect fluid transfer is declared, or subsequently performing the real-time PCR amplification in vessels only wherein a correct fluid transfer is declared.

13. The fluid transfer control method of claim 12, wherein the pre-defined volume of a second solution comprising a quencher molecule is transferred to the vessels prior to the step of measuring an intensity of the control dye.

14. The fluid transfer control method of claim 11, wherein the control dye and the detection dye are fluorescent dyes.

15. The fluid transfer control method of claim 12, wherein the control dye and the detection dye are fluorescent dyes.

16. The fluid transfer control method of claim 1, wherein the control dye is attached to an oligonucleotide.

17. The fluid transfer control method of claim 1, wherein the control dye and the quencher molecule are attached to oligonucleotides.

18. The fluid transfer control method of claim 12 wherein the control dye and the quencher molecule are attached to oligonucleotides.

19. The fluid transfer control method of claim 17, wherein the oligonucleotides have complementary sequences.

20. The fluid transfer control method of claim 18, wherein the oligonucleotides have complementary sequences.

* * * * *